(12) United States Patent
Vacic et al.

(10) Patent No.: US 11,287,436 B2
(45) Date of Patent: Mar. 29, 2022

(54) CARRIER FOR AUTOMATED MICROBIOLOGY SAMPLE PROCESSING (71) Applicant: SELUX DIAGNOSTICS, INC., Charlestown, MA (US)

(72) Inventors: Aleksandar Vacic, Charlestown, MA (US); Nathan Purmort, Charlestown, MA (US); Frederick P. Floyd, Jr., Charlestown, MA (US)

(73) Assignee: SELUX DIAGNOSTICS, INC, Charlestown, MA (US)

( * ) Notice: Subject to any disclaimer, the term of this patent is extended or adjusted under 35 U.S.C. 154(b) by 166 days.

(21) Appl. No.: 16/593,136

(22) Filed: Oct. 4, 2019

(65) Prior Publication Data

US 2020/0110105 A1 Apr. 9, 2020

Related U.S. Application Data

(60) Provisional application No. 62/741,830, filed on Oct. 5, 2018.

(51) Int. Cl.
*G01N 35/02* (2006.01)
*G01N 1/28* (2006.01)
*G01N 35/10* (2006.01)
*G01N 35/00* (2006.01)

(52) U.S. Cl.
CPC .............. *G01N 35/028* (2013.01); *G01N 1/28* (2013.01); *G01N 35/1011* (2013.01); *G01N 35/1095* (2013.01); *G01N 35/00732* (2013.01); *G01N 2035/00237* (2013.01); *G01N 2035/00277* (2013.01); *G01N 2035/00633* (2013.01); *G01N 2035/00831* (2013.01); *G01N 2035/00841* (2013.01)

(58) Field of Classification Search
None
See application file for complete search history.

(56) References Cited

U.S. PATENT DOCUMENTS

2002/0064867 A1 5/2002 Clark et al.
2003/0205511 A1* 11/2003 Olivier ................ B01L 3/50255
210/95

(Continued)

FOREIGN PATENT DOCUMENTS

WO 2018136859 A 7/2018

OTHER PUBLICATIONS

International Search Report and Written Application for International application No. PCT/US2019/054676, dated Mar. 5, 2020, 9 pages.

*Primary Examiner* — Kathryn Wright
(74) *Attorney, Agent, or Firm* — Kacvinsky Daisak Bluni PLLC (57) ABSTRACT

Carriers are provided for microbiological laboratory use, as are methods for their use. The carriers may be used to transport patient samples between laboratory stations and can be loaded into automated AST systems. In an aspect, a method of performing AST may include loading a tube comprising a patient sample onto a carrier. An AST panel may be loaded onto the carrier. The carrier may be conveyed to an automated inoculation assembly. The patient sample may be inoculated from the tube into the AST panel. The AST panel may be loaded into an automated AST system.

22 Claims, 7 Drawing Sheets

(56) References Cited

U.S. PATENT DOCUMENTS

2007/0020152 A1\* 1/2007 Costello, III .......... B01L 9/523
 422/400
2010/0111765 A1 5/2010 Gomm et al.
2018/0088141 A1 3/2018 Vacic et al.
2018/0284146 A1 10/2018 Hansen et al.

\* cited by examiner

FIG. 6

CARRIER FOR AUTOMATED MICROBIOLOGY SAMPLE PROCESSING

PRIORITY

This application claims the benefit to priority under 35 USC § 119 to U.S. Provisional Patent Application Ser. No. 62/741,830, filed Oct. 5, 2018, which is incorporated by reference herein in its entirety and for all purposes.

FIELD OF THE DISCLOSURE

This disclosure relates to mechanical devices for laboratory use.

BACKGROUND

Antimicrobials have transformed the practice of medicine, making once lethal infections more easily treatable and saving millions of lives. Quick administration of antimicrobials has been proven to reduce mortality especially in severe cases such as septicemia. In these severe cases, the most potent antimicrobials are used because information about organisms (e.g., species) is typically not known. These broad-spectrum antimicrobials can have serious side effects, cause organ damage, prolong recovery and hospital stays, and in some cases increase mortality. Furthermore, the overuse of antimicrobials has caused the rise of antimicrobial resistant organisms, which have become a serious and growing threat to public health. A growing body of evidence demonstrates that Antibiotic Stewardship Programs can optimize the treatment of infections and reduce adverse effects associated with antimicrobial use and misuse together with increased cure rates, reduced treatment failures, and increased percentage of correct therapy. By using targeted antimicrobial therapy, patient mortality can be reduced (e.g., minimized), recovery can be shortened, and hospitals can save money on both patient stay and minimizing usage of expensive antimicrobials.

The information needed for targeted antimicrobial therapy is most often delivered by a clinical microbiology facility, for instance in the form of antimicrobial susceptibility tests (AST). Historically, processes in clinical microbiology laboratories have been performed manually, and the adoption of automation in clinical microbiology labs has been slow compared to clinical chemistry and hematology areas where automation and new assay development have reduced time from sample to result. Accordingly, there are few end-to-end automated processes performed in clinical microbiology, and many workflows require laboratory personnel to perform manual operations and/or transfer samples between automated stations. Manual operations and sample transfers create the potential for user errors or contamination.

SUMMARY

This disclosure provides systems and methods for streamlining manual operations and sample transfers in clinical microbiology laboratories, reducing the risks of operator error or contamination in laboratory workflows.

In one aspect of this disclosure, a method of performing antimicrobial susceptibility testing may include loading a tube comprising a patient sample onto a carrier. An antimicrobial susceptibility testing (AST) panel may be loaded onto the carrier. The carrier may be conveyed to an automated inoculation assembly. A patient sample may be inoculated from the tube into the AST panel. The carrier may be conveyed to an automated AST system. The AST panel may be loaded into the automated AST system. The AST panel may be reloaded onto the carrier from the automated AST system following completion of an automated AST process. The carrier may be conveyed to a second laboratory station. Identifying information may be read and may be compared from the tube and from the AST panel. The method may be paused if the identifying information from the tube does not match the information from the AST panel. Identifying information may be read from the carrier and at least one of the tube and the AST panel. The identifying information of the carrier may be associated with the identifying information of at least one of the tube and the AST panel. The step of reading identifying information may include scanning a barcode.

In another aspect, an antimicrobial susceptibility testing system may include one or more containers each containing an array of sample wells. A carrier may be disposed under the containers. The carrier may include a stage space raised from a surface of the carrier. The stage space may have a stage perimeter smaller than an underside perimeter of each container. A stage protrusion may extend normal to the stage space and may extend into one of the containers.

In another aspect a method of performing AST may include loading a tube comprising a patient sample onto a carrier. An AST panel may be loaded onto the carrier. The carrier may be conveyed to an automated inoculation assembly. The patient sample may be inoculated from the tube into the AST panel. The AST panel may be loaded into an automated AST system.

In various embodiments, the AST panel may be reloaded onto the carrier from the automated AST system following completion of an automated AST process. The carrier may be conveyed to a second laboratory station. Identifying information from the tube and from the AST panel may be read and compared. The identifying information may be stored in a central database system that associates sample orders, accession numbers, panels and carriers. Identifying information from the tube may be paused if it does not correspond with the information from the AST panel. Identifying information may be read from the carrier and at least one of the tube and the AST panel, and associating the identifying information of the carrier with the identifying information of at least one of the tube and the AST panel. The step of reading identifying information may include scanning a barcode, reading an RFID tag, or reading an encoded magnetic pattern.

In another aspect, an AST system may include one or more containers each containing an array of sample wells. A carrier may be disposed under the containers that may include a first stage space raised from a surface of the carrier having a stage perimeter smaller than an underside perimeter of each container. A first stage protrusion may extend normal to the stage space and into one of the containers.

In various embodiments, a system may include additional stage protrusions, each stage protrusion corresponding with a corner of one of the containers. A second stage space may be adjacent the first stage space. A vessel may be disposed on the carrier adjacent the one or more containers. A vessel may include a plurality of vessel wells, each vessel well located within the vessel such that each vessel well is adjacent to a corresponding container such that no other container is between the corresponding container and the vessel well. A system may include a plurality of receptacles, each receptacle configured to accept a tube and each receptacle located within the vessel such that each receptacle is adjacent to a corresponding container such that no other container is between the corresponding container and the receptacle. Each receptacle of the plurality of receptacles may include a pin portion extending into the carrier configured to align the vessel with respect to the carrier. An alignment member may extend normal to the carrier and into the vessel. A system may include one or more slots disposed along an underside of the carrier configured to receive one or more arms for positioning the carrier.

In another aspect, a method of performing AST may include loading a patient sample onto a carrier. An AST panel may be loaded onto the carrier. The AST panel may be loaded into an automated AST system. A portion of the patient sample may be transferred to the AST panel. The patient sample may be identified to correspond with the AST panel. Identifying may include scanning a code associated with the patient sample. The patient sample may be selected from the group consisting of a positive blood culture and an isolate. The patient sample may be diluted by supplying a reagent.

DETAILED DESCRIPTION

Overview

Certain aspects of this disclosure encompass carriers (also referred to as trays) for carrying one or more microbiology patient samples. The carriers comprise one or more features to reduce the risk of contamination or user error during manual handling of patient samples. Carriers according to this disclosure may be used with any suitable patient sample vessels, including without limitation sample tubes and 96-, 384-, or 1536-, or any number-well plates or antimicrobial susceptibility testing (AST) panels. The carriers may include features for holding these vessels, such as recesses, sockets, tabs, and the like. Additionally, the carriers may include features to facilitate fluid handling, including fixed or removable fluid reservoirs, and features for holding such reservoirs like those listed above. Additionally, trays (e.g., carriers) may contain alignment features (e.g., datums), that can be added after carrier fabrication using a precise process (e.g. machining), for better alignment of AST panels during sample processing. As a machine places objects into contact with alignment features, the machine may register a collision and associate the collision with placing the object on a carrier. For example, the alignment members may provide tactile and/or machine-detectable detection of container misregistration and/or misalignment on the carrier.

It may be desirable in certain cases to attach identifying information for the one or more patient samples, for instance in the form of adhesive tags bearing text, numeral, or bar-coded identifiers of such sample. This is facilitated, in some embodiments, by the use of tabs or other structural elements to which tags may be permanently or temporarily adhered. In some cases, the tag is applied to a surface of the tray that is visible when the tray is loaded and/or is adjacent to a patient sample vessel. In other cases, the tag is applied to a surface of a patient sample vessel that is visible and/or accessible when the vessel is placed on the tray.

Carriers disclosed herein may also be stackable, storable, or mateable with other carriers of the same or different type and other structures, including without limitation automated lab stations, storage racks, etc. This may be facilitated by the inclusion of pins, flanges, or like features that are sized to fit with complementary structures.

Turning now to FIGS. 1A-e, which depict one exemplary embodiment of this disclosure, a sample carrier 100 includes four stage spaces 110 for receiving containers 120 comprising patient samples, such as multi-well plates (e.g., 96-well or 384-well plates) and/or AST sample panels. The spaces 110 are raised from a surface of the carrier 100 and have a stage perimeter 111 that is smaller than an underside perimeter of each container 120. The spaces 110 also include one or more stage protrusion internal alignment features 112, such as flanges, that fit within e.g., a skirt of a multi-well plate or AST panel. In various embodiments, the alignment features 112 may vary in height and/or shape (e.g. one or more beveled corners conforming to the shape of the underside of a container 120) that may provide a rotational alignment feature for the containers 120, assisting with orienting the containers 120 to a location and, e.g., not 180° out of rotation.

Carrier 100 further includes a vessel 130 for receiving a fluid. The vessel 130 comprises four wells 132, each well 132 corresponding to each of the four patient sample containers 120. The fluid vessel 130 is positioned in the center of the carrier 100 adjacent the sample containers 120, and each well 132 is generally elongated, with a tapering cross-section such that the bottom of each well 132 is narrower than the top. The wells 132 are positioned such that a fluid handling device, such as an automated or manual pipettor, is moveable directly between each well 132 and its corresponding container 120 without the need to pass over any other container 120 in the carrier 100. This arrangement reduces the potential for contamination during fluid handling operations. The carrier 100 also includes first and second flanges 140 that can be gripped by a user.

The carrier 100 or the fluid vessel 130 can also include one or more receptacles 150 for a sample tube, which are inserted or molded into position to correspond to the sample container 120. For instance, the receptacles 150 can contain tubes for patient samples inoculated into each of the patient sample containers 120.

Figure 1A:
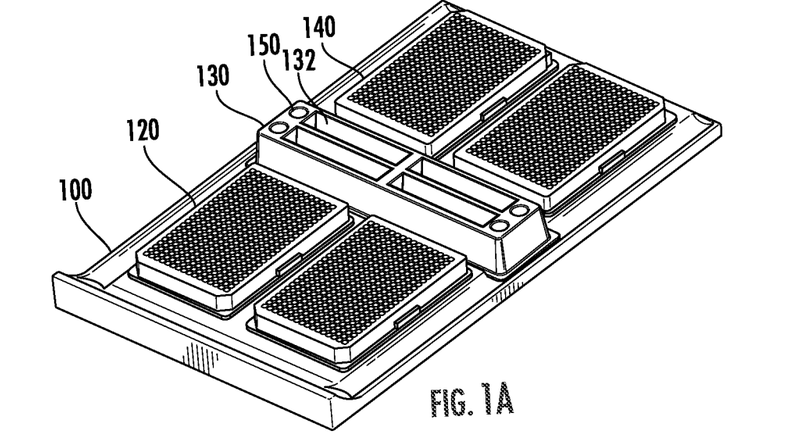
FIGS. 1A, 1B, 1C, 1D, and 1E depict perspective and elevation views of an exemplary patient sample carrier, in accordance with an embodiment of the present disclosure.
Figure 1B:
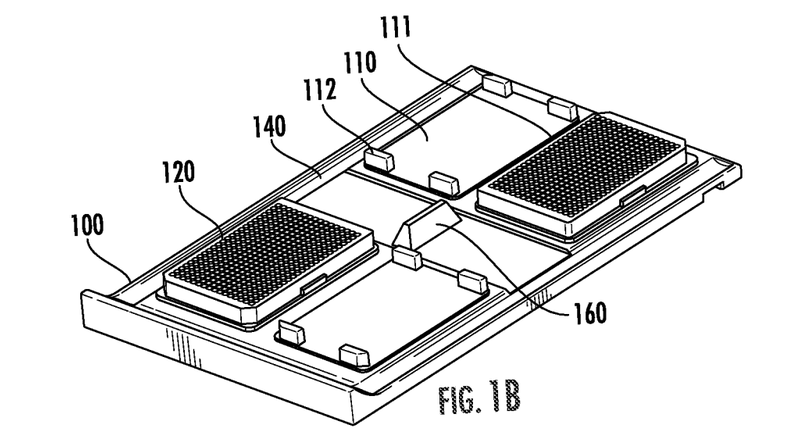

FIG. 1B shows one embodiment in which the fluid vessel 130 is removably disposed on the carrier 100 by means of an alignment member 160, positioned to fit into a space on the underside of the fluid vessel 130.

Figure 1C:
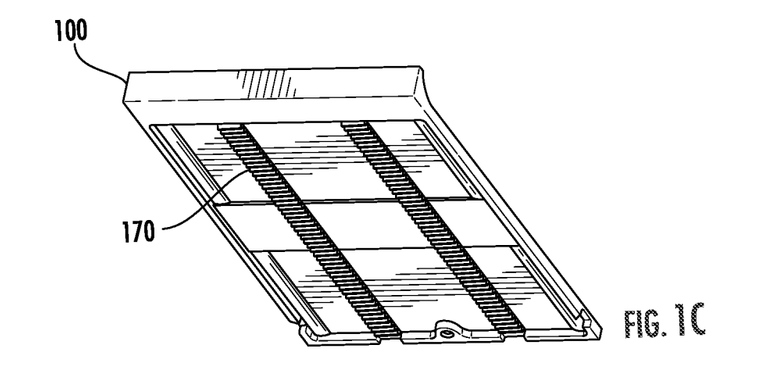
Figure 1D:
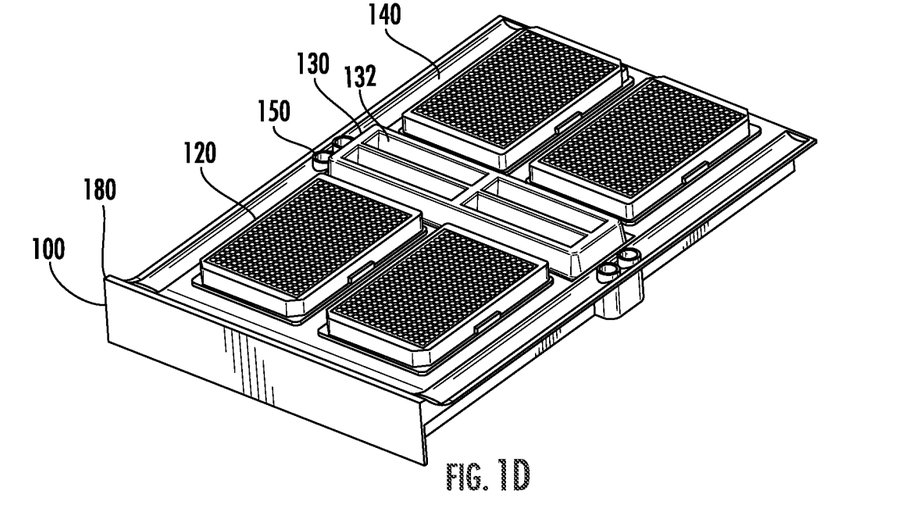
Figure 1E:
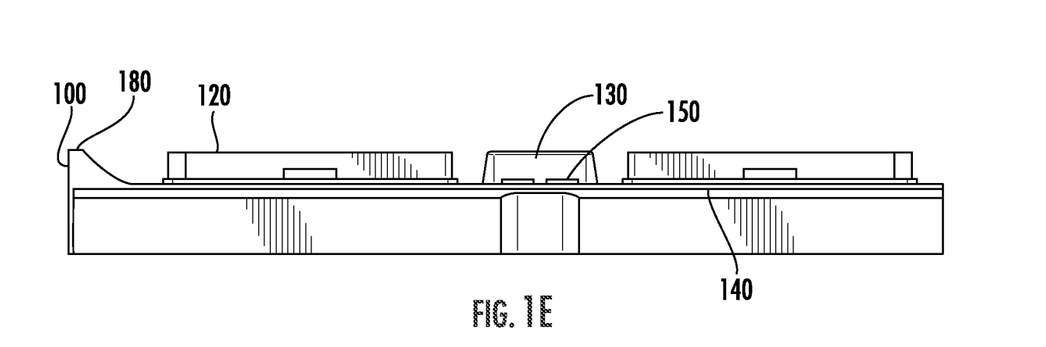

FIG. 1C depicts an underside of the carrier 100, which includes two slots 170 for receiving mechanical members of, e.g., a rack or automated system which moves, retracts, and/or advances or ejects the carrier 100. FIGS. 1D and 1E show a carrier 100 that can be inserted into a rack or automated system, which is asymmetrical and defines a sidewall 180, that, for example, is positioned opposite of the end of the carrier 100 that is inserted into the rack or automated system. The sidewall may have a height that is just taller than the height of a patient sample container 120 and/or a sample tube that is positioned in the carrier 100, reducing the risk of mechanical interference between a rack or automated system and the contents of a carrier 100.

Figure 2A:
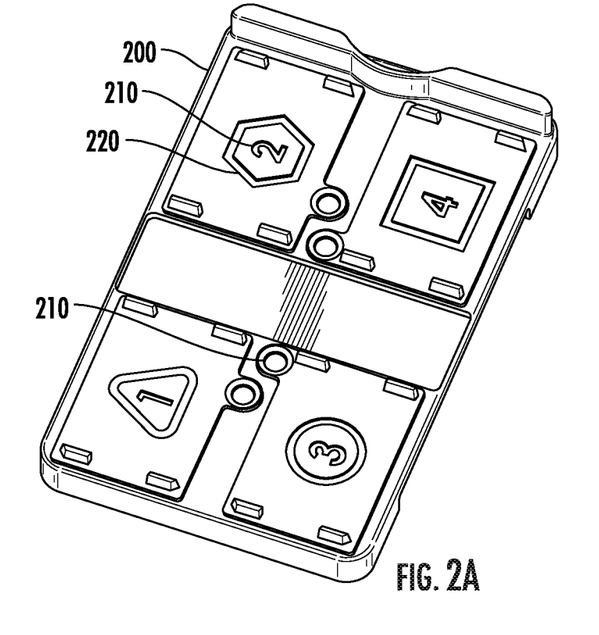
FIGS. 2A and 2B depict perspective views of another exemplary patient sample carrier, in accordance with an embodiment of the present disclosure.
Figure 2B:
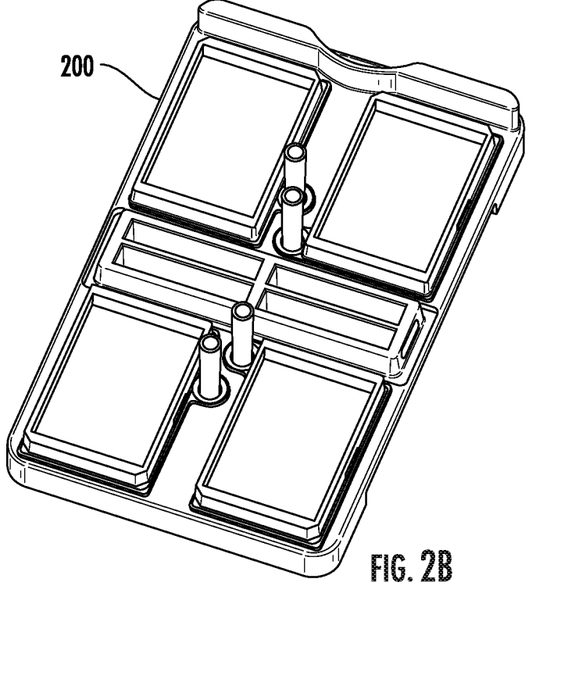

Turning now to FIGS. 2A and 2B, another exemplary design for a sample carrier is depicted. The carrier 200 is similar to the carrier 100 depicted in FIGS. 1A-1E and also incorporates color-coded and engraved or molded numerals 210 and symbols 220, to demarcate positions for fluid sample containers and tubes corresponding to the patient samples inoculated into the sample containers.

Figure 3A:
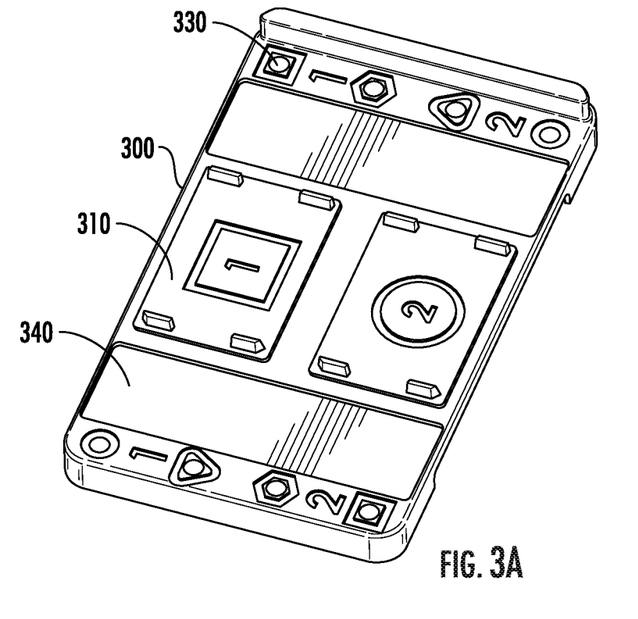
FIGS. 3A and 3B depict perspective views of still another exemplary patient sample carrier, in accordance with an embodiment of the present disclosure.
Figure 3B:
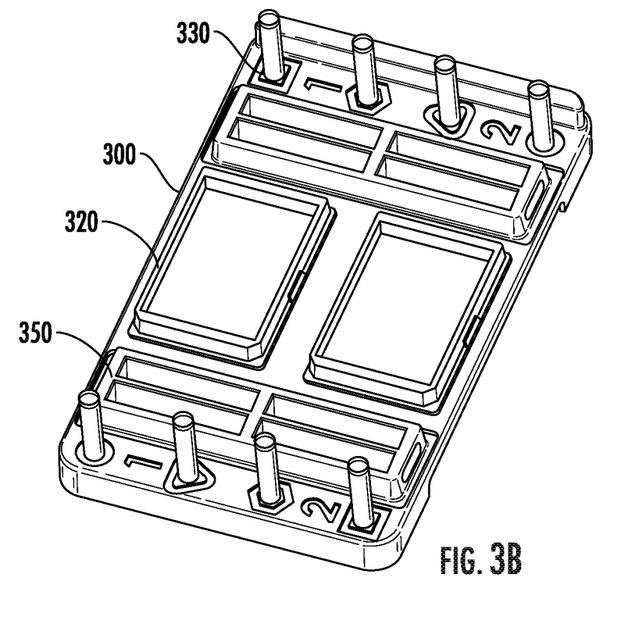

The carrier designs presented above are well suited to conditions where a single well of a fluid carrier and a single sample vessel each correspond to a single container. However, in some instances, it may be desirable to have multiple wells of a fluid vessel and/or multiple sample tubes corresponding to a single patient sample container. For instance, in the embodiment depicted in FIGS. 3A and 3B, a carrier 300 contains two spaces 310 for two patient sample containers 320 and contains eight positions 330 for four patient sample tubes, with four positions 330 corresponding to each sample container 320, as indicated by color coding and/or engraved numerals and/or symbols. The carrier 300 also includes two spaces 340 for two fluid containers 350, providing up to four wells for each sample container 320.

Figure 4A:
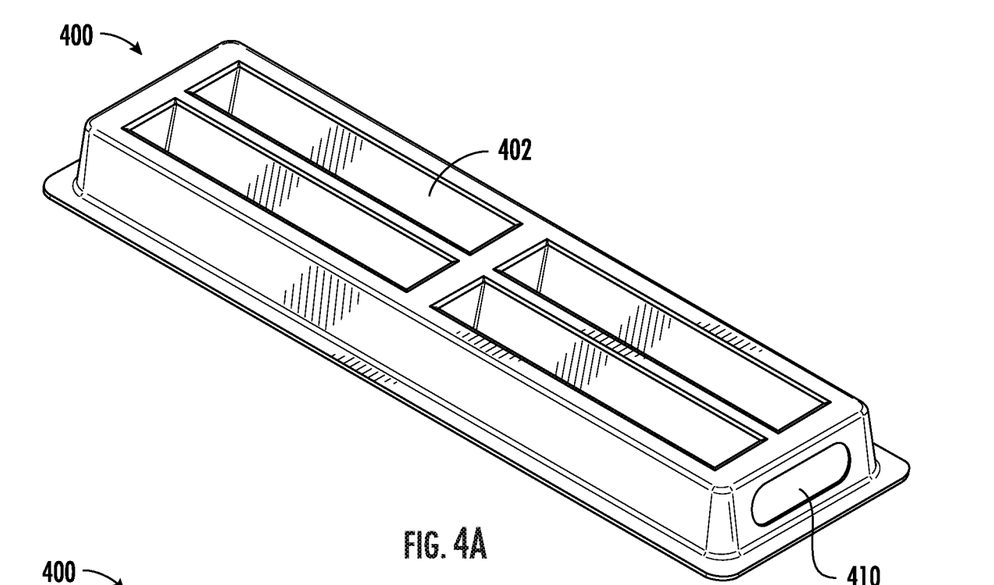
FIGS. 4A and 4B depict perspective views of fluid containers according to embodiments of the present disclosure.
Figure 4B:
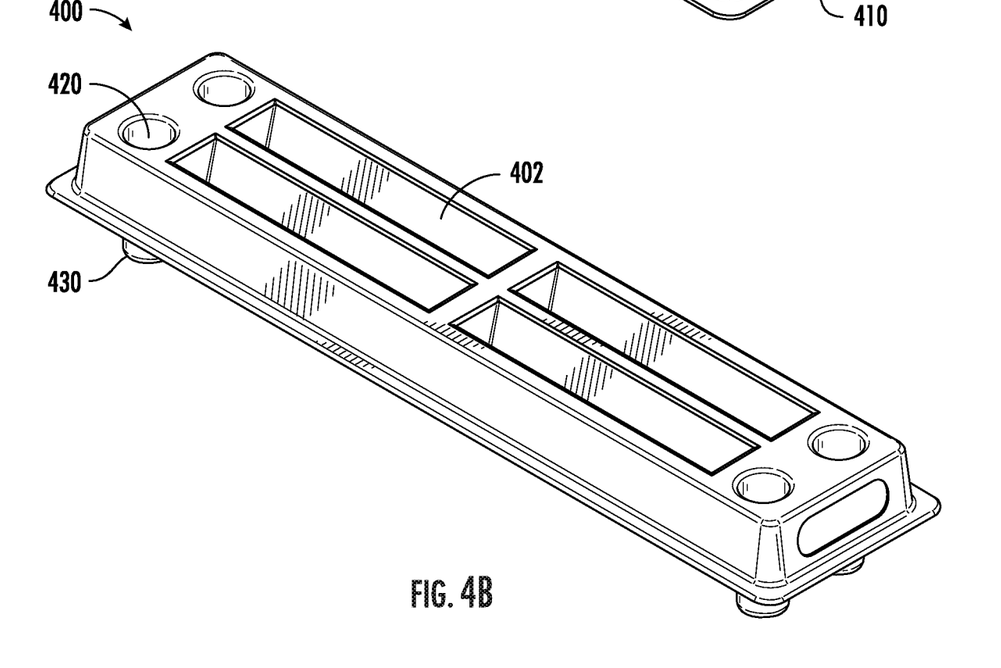

FIGS. 4A and 4B depict two alternate designs for fluid vessels 400 illustrating, variously, the inclusion of one or more indented or textured regions 410 to assist a user in gripping the fluid container 400 to attach or remove it from the fluid container 400; and the inclusion of integrated sample tube positions 420 and pins 430 insertable into a sample carrier to secure the fluid container 400 thereto. Vessel wells 402 may contain one or more fluids for mixing, transferring, or diluting within a carrier. Although four vessel wells 402 are illustrated, any number of vessel wells may be employed, e.g., one, two, three, five, eight, ten, twenty, fifty, etc.

Figure 5A:
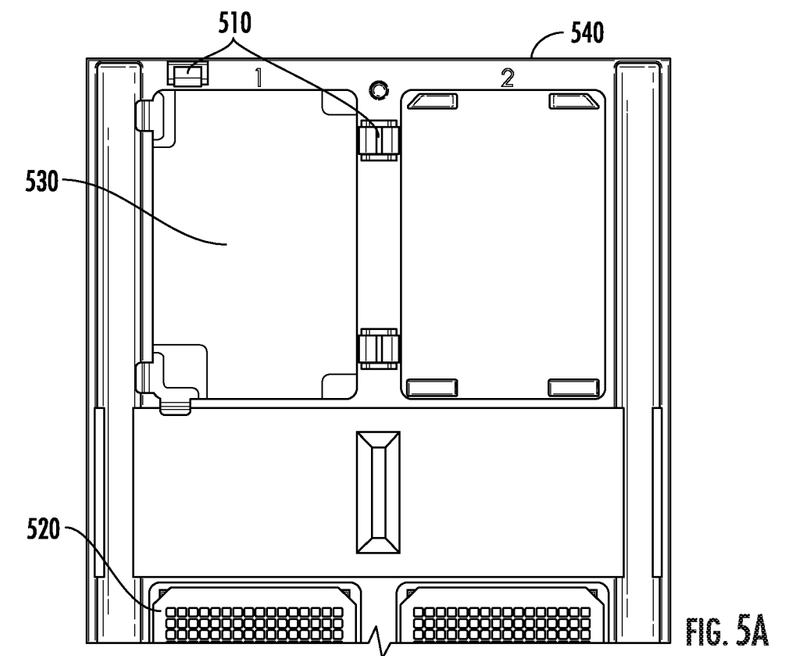
FIGS. 5A and 5B illustrate structures for retaining patient sample containers according to embodiments of the present disclosure.
Figure 5B:
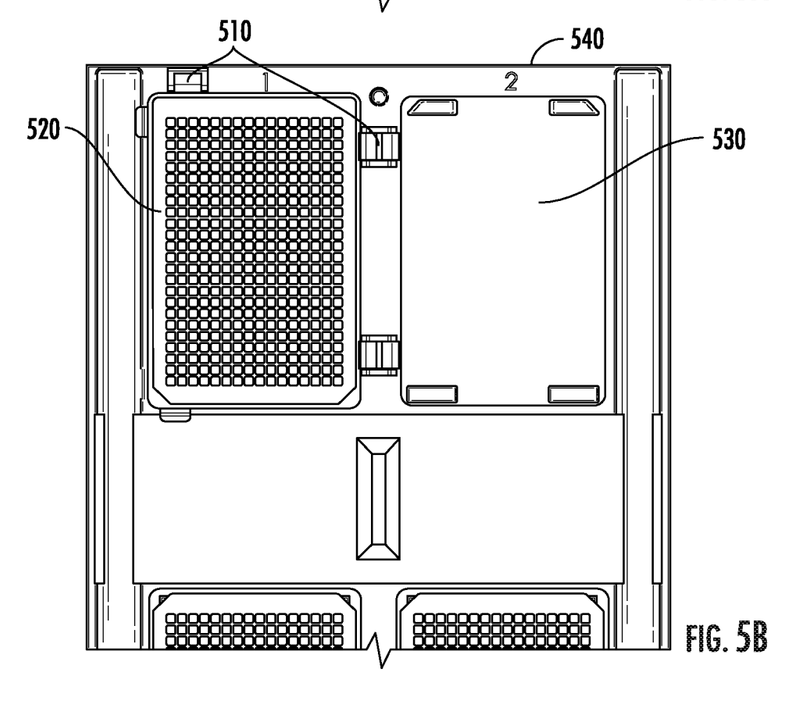

Carriers of this disclosure may include a plurality of clips 510 to retain and/or align each patient sample container, for instance as shown in FIGS. 5A and 5B. In some embodiments, the clips 510 are positioned along two edges of a sample container 520 so as to press the sample container 520 toward an edge of a space 530 in a carrier 540. In various embodiments, a space 530 may have an asymmetrical outer perimeter (e.g., one or more chamfered corners) and/or may be oriented in a different direction than one or more other spaces 530 such that sample containers 520 can be oriented in a limited number of directions over the space 530 (e.g., a space 530 may have its top-left corner chamfered while another space 530 may have a corresponding top-left corner not chamfered while another corner is instead chamfered). Alignment of the sample container 520 is also facilitated by the use of one or more tabs, flanges or pins positioned to interact with a sidewall or an underside of the patient sample container 520.

In use, carriers of this disclosure may be used to move patient samples between clinical laboratory stations, such as culturing stations to produce positive blood cultures or isolates, inoculators, AST testing systems, mass-spectrometry systems, etc. In one exemplary workflow, one or more patient sample tubes, each comprising a patient sample for testing, is inserted into an opening on the carrier, and a patient sample container (e.g., an AST panel) that will be inoculated with the patient sample is loaded into an opening corresponding to the patient sample container, as indicated by corresponding color-coding and/or corresponding numerals or symbols. The patient sample tube, the sample container, and/or the carrier is optionally marked, e.g., with an adhesive patient identifier such as a bar code or the like. The identifiers of the sample tube, sample container, the carrier, and/or the vessel may be identified and associated with each other. For example, a sample tube may be identified by scanning a code, and the sample tube may be placed onto a carrier. A code for the carrier may be scanned such that the code of the tube and the code of the carrier are associated with each other. An identifying code on a container and/or a vessel may be scanned, and a user interface may indicate to a user where to place the container, e.g., adjacent to an associated sample tube.

The carrier is then conveyed, manually or automatically, to an automated inoculator, into which the patient sample tube and the corresponding patient sample container are inserted and the sample container is inoculated. The sample tube and sample container are then removed, and the inoculation process is repeated for each sample tube/sample container on the carrier.

Either before or after inoculation, the wells of the fluid container are filled, e.g., with a broth solution for microbial growth, and fluid is transferred, e.g., by manual pipetting or automated fluid handling system, from a well of the fluid container into a corresponding sample container. This may include diluting of fluids by adding one or more reagents that may be supplied from the automated system or a user. These steps may be repeated for each fluid well and sample container until all containers on the carrier are loaded. Afterward, any fluid remaining in the wells is optionally removed, e.g., by removing the container and decanting its contents, or aspirating fluid from the wells.

The carrier is then conveyed, again either manually or automatically, to an incubation and/or agitation system. The incubation/agitation system may be a stand-alone system or part of a larger system such as an automated AST system. In some cases, the carrier is loaded directly into the incubation/agitation system, which is then operated to incubate the sample containers under conditions conducive to microbial growth. Alternatively, the sample containers may be removed from the remaining sample carrier and loaded directly into the incubation/agitation system. In this instance, the sample tubes and/or the entire carrier may be placed in a refrigerated environment (e.g, a refrigerated rack) for storage during processing of the sample container. A sample container may also be conferred from a loaded carrier to a fluidics or other processing station (e.g. optical measurement station) prior to being loaded into the incubation/agitation system.

Once the incubation/agitation process is complete, or once processing of the patient sample container by the automated system is complete, the sample containers are returned to their positions on the carrier, if they were removed, and the carrier is conveyed to another laboratory station for further processing or analysis, until the desired laboratory analysis process is complete. Afterward, the carrier and its contents may be stored, e.g., in refrigerated conditions, until the results of the laboratory analysis are processed, validated, etc., or for a predetermined interval (e.g., 1 day, 1 week, etc.). Alternatively, the contents of the carrier may be disposed of, and the carrier itself may be disposed of or may be recycled, sterilized, etc.

At one or more points in the workflow, identifying information on the sample tube, patient sample container and the tray itself may be viewed and compared, to ensure samples remain matched during the workflow. For instance, a barcode may be scanned on one or more of the patient sample tubes and the patient sample container, and is associated with a specific tray by its barcode. This may be done at or prior to the inoculation stage, and upon insertion into or removal from the automated system. At the end of a workflow, barcodes on the sample tube, sample container and/or the carrier may be scanned to indicate that processing is complete, and that the samples may be placed into storage while the carrier may be released for reuse. The identifying information may be stored in a central database system that associates sample orders, accession numbers, panels, and carriers.

Figure 6:
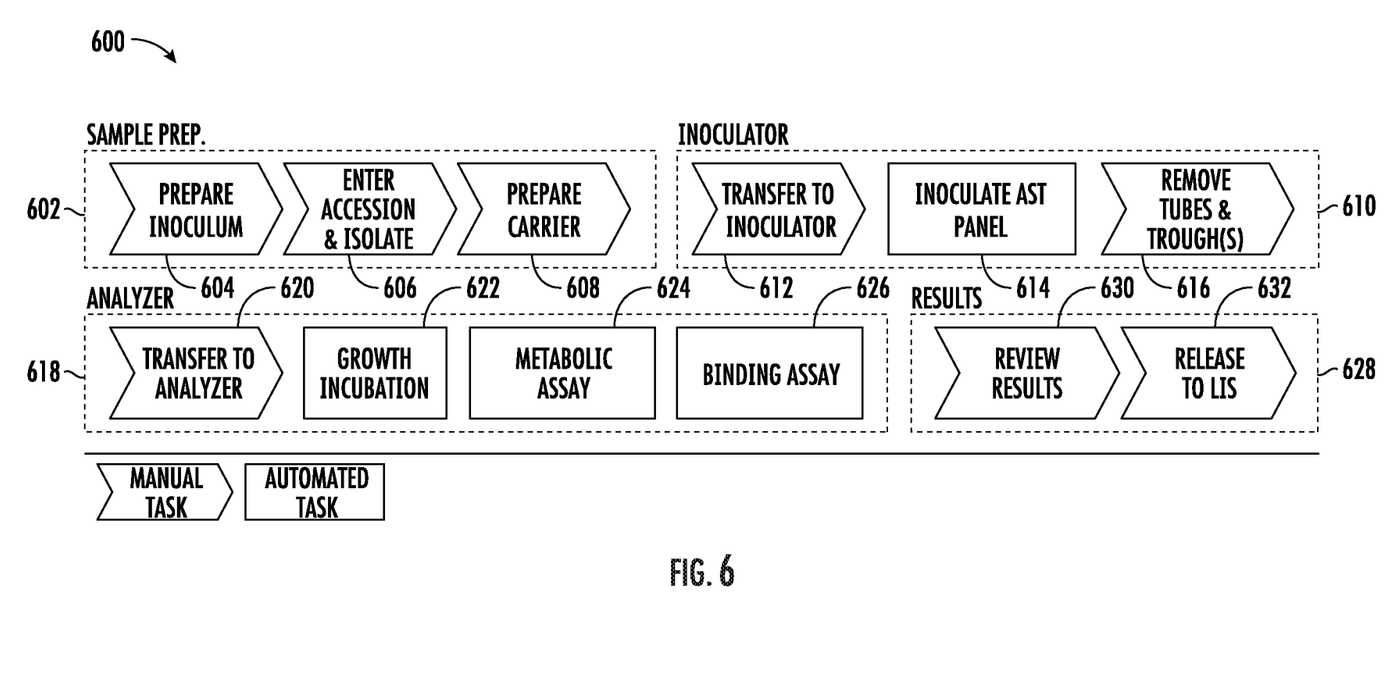
FIG. 6 illustrates a method of performing AST according to an embodiment of the present disclosure.

Referring to FIG. 6, a method 600 of performing AST may include a sample preparation step 602. A user may prepare 604 a cultured bacteria for AST testing, entering accession and isolation 606. The user may prepare a carrier 608 by capturing sample information and pairing each sample with an appropriate AST panel grouped onto the carrier for transfer to and from the processing equipment. In the Inoculator step 610, the user may transfer 612 the carrier into an instrument and initiates an automated Inoculation sequence 614. When complete, the user removes 616 the carrier, places lids on the AST panels and may remove the sample tubes and vessel wells (i.e., dilution troughs). In the analyzer step 618, the user transfers the carrier into the instrument and initiates the automated AST testing sequence. After the bacteria have been incubated 622 to reach a sufficient concentration, as detected automatically with an assay 624 (e.g. a "sufficient growth assay"), the analyzer 618 automatically processes the two sequential AST assays, the metabolic assay 624 followed by a binding assay 626. Upon completion, results 628 may be presented to the user for review 630 and release 632 to an LIS.

This overview has focused on a handful of exemplary embodiments that illustrate the principles of certain microbiology laboratory sample carriers, and of laboratory processes utilizing such carriers. The disclosure is intended to encompass modifications and variations that will be evident to those of skill in the art.

CONCLUSION

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Those skilled in the art will recognize or be able to ascertain using no more than routine experimentation, multiple equivalents to the specific embodiments described herein. Such equivalents are intended to be encompassed by the following claims.

What is claimed is:

1. A carrier for antimicrobial susceptibility testing (AST) panels, fluid troughs, and sample tubes comprising:
   (a) one or more first stage spaces for an AST panel, wherein each first stage space comprises
      (i) a stage space raised from a surface of the carrier having a stage perimeter smaller than an underside perimeter of each panel, and
      (ii) at least one protrusion within said first stage space and extending normal to the stage space for engaging said panel;
   (b) one or more second stage spaces for a fluid trough, wherein each second stage space comprises
      (i) a stage space raised from a surface of the carrier having a stage perimeter smaller than an underside perimeter of each fluid trough, and
      (ii) at least one protrusion within said first stage space and extending normal to the stage space for engaging said trough; and
   (c) one or more receptacles configured to accept a sample tube, wherein said receptacles are located on said carrier or said carrier further comprises at least one fluid trough comprising one or more receptacles configured to accept a sample tube, wherein said first stage spaces, said second stage spaces and said receptacles are arranged on said carrier so that a fluid handling device is moveable directly between a panel and a tube without the need to pass over any other panel.

2. The carrier of claim 1, wherein said first stage spaces, said second stage spaces and said receptacles are arranged on said carrier such that
   (a) the one or more second stage spaces are adjacent to and between at least two first stage spaces, and wherein the fluid trough comprises the one or more receptacles;
   (b) the one or more second stage spaces are adjacent to and between at least two first stage spaces, and wherein the one or more receptacles are disposed along a perimeter of the carrier and the one or more receptacles are adjacent to the one or more second stage spaces;
   (c) the one or more second stage spaces are adjacent to and between at least two first stage spaces, and wherein the one or more receptacles are disposed between one of the at least two first stage spaces and a third stage space; or
   (d) the one or more first stage spaces are adjacent to and between two second stage spaces, and wherein one of the two second stage spaces is adjacent to the one or more receptacles.

3. A method of performing antimicrobial susceptibility testing (AST), comprising the steps of:
   loading a tube comprising a patient sample onto a carrier of claim 1;
   loading an AST panel onto the carrier;
   conveying the carrier to an automatic inoculator;
   inoculating the patient sample from the tube into the AST panel; and
   loading the AST panel into an automated AST system.

4. The method of claim 3, further comprising the step of reloading the AST panel onto the carrier from the automated AST system following completion of an automated AST process, and conveying the carrier to a second laboratory station.

5. The method of claim 3, further comprising:
   reading and comparing identifying information from the tube and from the AST panel; and
   storing the identifying information in a central database system that associates sample orders, accession numbers, panels and carriers.

6. The method of claim 5, further comprising pausing the method if the identifying information from the tube does not correspond with the information from the AST panel.

7. The method of claim 3, further comprising the step of reading identifying information from the carrier and at least one of the tube and the AST panel, and associating the identifying information of the carrier with the identifying information of at least one of the tube and the AST panel.

8. The method of claim 7, wherein the step of reading identifying information comprises scanning a barcode, reading an RFID tag, or reading an encoded magnetic pattern.

9. An antimicrobial susceptibility testing (AST) system comprising:

one or more containers each containing an array of sample wells; and a carrier of claim 1 disposed under the one or more containers.

10. The AST system of claim 9, further comprising additional stage protrusions, each stage protrusion corresponding with a corner of one of the containers.

11. The AST system of claim 9, further comprising a second stage space adjacent the first stage space.

12. The AST system of claim 9, further comprising a vessel disposed on the carrier adjacent the one or more containers.

13. The AST system of claim 12, wherein the vessel further comprises a plurality of vessel wells, each vessel well located within the vessel such that each vessel well is adjacent to a corresponding container such that no other container is between the corresponding container and the vessel well.

14. The AST system of claim 12, further comprising a plurality of receptacles, each receptacle configured to accept a tube and each receptacle located within the vessel such that each receptacle is adjacent to a corresponding container such that no other container is between the corresponding container and the receptacle.

15. The AST system of claim 14, wherein each receptacle of the plurality of receptacles comprises a pin portion extending into the carrier configured to align the vessel with respect to the carrier.

16. The AST system of claim 12, further comprising an alignment member extending normal to the carrier and into the vessel.

17. The AST system of claim 9, further comprising one or more slots disposed along an underside of the carrier configured to receive one or more arms for positioning the carrier.

18. A method of performing antimicrobial susceptibility testing (AST), comprising the steps of:

loading a patient sample onto a carrier of claim 1;

loading an AST panel onto the carrier;

loading the AST panel into an automated AST system; and transferring a portion of the patient sample to the AST panel.

19. The method of claim 18, further comprising identifying that the patient sample corresponds with the AST panel.

20. The method of claim 19, wherein identifying includes scanning a code associated with the patient sample.

21. The method of claim 18, wherein the patient sample is selected from the group consisting of a positive blood culture and an isolate.

22. The method of claim 18, further comprising diluting the patient sample by supplying a reagent.

\* \* \* \* \*